US011388789B2

(12) United States Patent
Nickles et al.

(10) Patent No.: US 11,388,789 B2
(45) Date of Patent: Jul. 12, 2022

(54) METHOD FOR CONTROLLING OPERATION OF A LIGHTING SYSTEM HAVING HIGH INTENSITY NARROW SPECTRUM LIGHT SOURCES

(71) Applicant: Hubbell Lighting, Inc., Shelton, CT (US)

(72) Inventors: Blake Ashton Nickles, Greenville, SC (US); Nathaniel Stephen Hack DeVol, Greenville, SC (US); Leslie Anne Cade, Mauldin, SC (US)

(73) Assignee: Hubbell Lighting, Inc., Shelton, CT (US)

( * ) Notice: Subject to any disclaimer, the term of this patent is extended or adjusted under 35 U.S.C. 154(b) by 146 days.

(21) Appl. No.: 16/800,086

(22) Filed: Feb. 25, 2020

(65) Prior Publication Data
US 2020/0305248 A1    Sep. 24, 2020

Related U.S. Application Data

(60) Provisional application No. 62/819,859, filed on Mar. 18, 2019.

(51) Int. Cl.
*H05B 45/12* (2020.01)
*H05B 47/115* (2020.01)
(Continued)

(52) U.S. Cl.
CPC ........... *H05B 45/12* (2020.01); *A61L 2/00* (2013.01); *A61L 2/084* (2013.01); *A61L 2/10* (2013.01); *H05B 45/48* (2020.01); *H05B 47/115* (2020.01)

(58) Field of Classification Search
CPC ........ H05B 45/12; H05B 45/48; H05B 47/10; H05B 47/105; H05B 47/11; H05B 47/115;
(Continued)

(56) References Cited

U.S. PATENT DOCUMENTS 3,926,556 A    12/1975    Boucher
4,910,942 A    3/1990    Dunn et al.
(Continued)

FOREIGN PATENT DOCUMENTS

WO    WO2007012875    2/2007

OTHER PUBLICATIONS

MacLean et al., "405 nm light technology for the inactivation of pathogens and its potential role for environmental disinfection and infection control," *The Journal of Hospital Infection*, Sep. 2014, vol. 88, Issue 1—27 pages.
(Continued)

*Primary Examiner* — Abdullah A Riyami
*Assistant Examiner* — Syed M Kaiser
(74) *Attorney, Agent, or Firm* — Michael Best & Friedrich LLP

(57) ABSTRACT

A method for controlling operation of a lighting system is provided. The method includes operating the lighting system in a first mode during a time period to provide a first light output. The first output can be a blend of HINS light and non-HINS light. The method includes determining a dosage amount of HINS light provided during the time period. Furthermore, the method includes operating the lighting system in a second mode to provide a second lighting output. The second light output can be HINS light or a blend of HINS light and non-HINS light. Furthermore, spectral energy associated with HINS light in the second light output is greater than spectral energy associated with the HINS light in the first light output.

18 Claims, 10 Drawing Sheets

(51) Int. Cl.
  *H05B 45/48* (2020.01)
  *A61L 2/00* (2006.01)
  *A61L 2/10* (2006.01)
  *A61L 2/08* (2006.01)

(58) Field of Classification Search
  CPC ... A61L 2/08; A61L 2/084; A61L 2/24; A61L 9/20
  See application file for complete search history.

(56) References Cited

U.S. PATENT DOCUMENTS

| | | | |
|---|---|---|---|
| 6,251,127 | B1 | 6/2001 | Biel |
| 6,967,008 | B1 | 11/2005 | Barnes |
| 8,398,264 | B2 | 3/2013 | Anderson et al. |
| 9,039,966 | B2 | 5/2015 | Anderson et al. |
| 9,333,274 | B2 | 5/2016 | Peterson et al. |
| 9,439,989 | B2 | 9/2016 | Lalicki et al. |
| 9,642,358 | B2 | 5/2017 | Cai et al. |
| 9,700,641 | B2 | 7/2017 | Hawkins et al. |
| 9,927,097 | B2 | 3/2018 | Lalicki et al. |
| 10,617,774 | B2* | 4/2020 | Winslow .................... F21V 9/30 |
| 10,728,987 | B1* | 7/2020 | Westrick, Jr. ......... H05B 47/105 |
| 2003/0188740 | A1* | 10/2003 | Tribelsky ................. A61P 37/02 128/200.14 |
| 2004/0039242 | A1 | 2/2004 | Tolkoff et al. |
| 2005/0049228 | A1 | 3/2005 | Albrecht et al. |
| 2005/0055070 | A1 | 3/2005 | Jones et al. |
| 2005/0107849 | A1 | 5/2005 | Altshuler et al. |
| 2006/0085052 | A1 | 4/2006 | Feuerstein et al. |
| 2008/0137066 | A1 | 6/2008 | Weinstein |
| 2009/0076115 | A1 | 3/2009 | Wharton et al. |
| 2009/0168396 | A1 | 7/2009 | Moriyasu et al. |
| 2009/0183523 | A1 | 7/2009 | Willette |
| 2009/0267485 | A1* | 10/2009 | Nagatomi .......... C09K 11/7734 313/503 |
| 2010/0208054 | A1 | 8/2010 | Farr |
| 2010/0246169 | A1 | 9/2010 | Anderson et al. |
| 2011/0227487 | A1 | 9/2011 | Nichol et al. |
| 2011/0256019 | A1 | 10/2011 | Gruen et al. |
| 2013/0120678 | A1* | 5/2013 | Chao ........................ F21K 9/60 349/34 |
| 2013/0293156 | A1 | 11/2013 | Wells |
| 2014/0060096 | A1 | 3/2014 | Shur |
| 2014/0220652 | A1* | 8/2014 | Gonzalez ............... B01D 53/84 435/167 |
| 2016/0015840 | A1 | 1/2016 | Gordon |
| 2016/0030609 | A1 | 2/2016 | Peterson et al. |
| 2016/0030610 | A1 | 2/2016 | Peterson et al. |
| 2016/0120410 | A1 | 5/2016 | Kim |
| 2016/0339203 | A1 | 11/2016 | Krames et al. |
| 2016/0361229 | A1 | 12/2016 | Na |
| 2016/0375161 | A1 | 12/2016 | Hawkins et al. |
| 2016/0375162 | A1 | 12/2016 | Marry et al. |
| 2016/0375163 | A1 | 12/2016 | Hawkins |
| 2017/0006685 | A1 | 1/2017 | Barron et al. |
| 2017/0034889 | A1 | 2/2017 | Primous et al. |
| 2017/0080117 | A1 | 3/2017 | Gordon |
| 2017/0101328 | A1 | 4/2017 | Smetona et al. |
| 2017/0246329 | A1 | 8/2017 | Lloyd |
| 2018/0117189 | A1* | 5/2018 | Yadav ....................... A61L 2/24 |
| 2018/0117190 | A1 | 5/2018 | Bailey |
| 2018/0117193 | A1 | 5/2018 | Yadav et al. |
| 2018/0121703 | A1 | 5/2018 | Jung |
| 2018/0124883 | A1 | 5/2018 | Bailey |
| 2018/0225498 | A1 | 8/2018 | Setlak |
| 2018/0311386 | A1* | 11/2018 | Hawkins ................. F21V 29/70 |
| 2018/0326104 | A1 | 11/2018 | Hawkins et al. |

OTHER PUBLICATIONS

MacLean et al., "An Innovation: Decontamination by Light—HINS-light Environmental Decontamination System, A new method for pathogen control in the clinical environment," Microsoft Power Point, HINS-light EDS Presentation for Infection Prevention Scotland, The Robertson Trust Laboratory for Electronic Sterilisation Technologies (ROLEST), Oct. 27, 2010—20 pages.

Noimark et al., "Light-activated antimicrobial surfaces with enhanced efficacy induced by a dark-activated mechanism," Chemical Science, Issue 6. June 1. 2014—1 page.

Wallace, John "HINS light kills surface bacteria in hospitals," Laser Focus World, http://www.laserfocusworld.com/articles/2010/11/hins-light-kills-surface.html. accessed on Oct. 30, 2017, PennWell Corporation, Tulsa, OK, Nov. 15, 2010—2 pages.

MacLean et al., Environmental decontamination of a hospital isolation room using high-intensity narrow-spectrum light, The Hospital Infection Society, Elsevier Ltd., Nov. 2010:76(3)—1 page.

Kenall Mfg. Launches New Bacteria-killing LED Light for Hospitals, LEDinside, a Business Division of TrendForce Corp., Jun. 29, 2015, accessed on Oct. 30, 2017, http://www.ledinside.com/products/2015/6/kenall_manufacturing_launches_new_uv_led_light_for_hospitals—3 pages.

Nitzan et al. "ALA induced photodynamic effects on Gram positive and negative bacteria," *Photochem. Photobiol. Sci.*, 2004, 3—18 pages.

MacLean "An Investigation Into the Light Inactivation of Medically Important Microorganisms," University of Strathclyde, 2006—260 pages.

Nitzan et al., "Endogenous Porphyrin Production in Bacteria by Aminolaevulinic Acid and Subsequent Bacterial Photoeradication," *M. Lasers Med Sci* (Dec. 1999) vol. 14, Issue 4, pp. 269-277.

Ashkenazi et al., "Eradication of Propionibacterium acnes by its endogenic porphyrins after illumination with high intensity blue light," *FEMS Immunology & Medical Microbiology*, vol. 35, Issue 1, Jan. 1, 2003, pp. 17-24.

Ganz et al., "*Helicobacter pylori* in Patients Can Be Killed by Visible Light," *Lasers Surg Med.*, Apr. 2005; 36(4): pp. 260-265.

Møller et al., "How Finsen's light cured lupus vulgaris," *Photodermatol Photoimmunol Photomed* 2005; 21: pp. 118-124.

Kjeldstad, "Photoinactivation of Propionibacterium acnes bv Near-Ultraviolet Light," *Zeitschrift für Naturforschung C*, vol. 39, Issue 3-4, 1984, pp. 300-302.

Derosa et al., "Photosensitized singlet oxygen and its applications," *Coordination Chemistry Reviews*, vols. 233-234, Nov. 1 2002, pp. 351-371.

Elman et al., "The effective treatment of acne vulgaris by a high-intensity, narrow band 405-420 nm light source," *J Cosmetic & Laser Ther* 2003; 5: pp. 111-116.

Konig et al., "Red Light Kills Bacteria via Photodynamic Action," abstract, *Cellular and molecular biology*, 46(7):1297-303, Dec. 2000—1 page.

Philipp-Dormston et al., "Comparison of Porphyrin and Heme in Various Heterotrophic Bacteria," Abstract, *Enzyme* 16(1):57-64 • Feb. 1973—1 page.

PCT/US2020/019604 International Search Report and Written Opinion dated Jun. 8, 2020 (10 pages).

* cited by examiner

METHOD FOR CONTROLLING OPERATION OF A LIGHTING SYSTEM HAVING HIGH INTENSITY NARROW SPECTRUM LIGHT SOURCES

PRIORITY CLAIM

The present application claims the benefit of priority of U.S. Provisional App. No. 62/819,859, titled "Method for Controlling Operation of a Lighting System Having High intensity Narrow Spectrum Light Sources," having a filing date of Mar. 18, 2019, which is incorporated by reference herein.

FIELD

The present subject matter relates generally to lighting systems.

BACKGROUND

Lighting systems can be used to provide illumination of spaces and objects for a variety of different applications. In some lighting systems, high intensity narrow spectrum (HINS) light can be used to reduce, suppress, or inactivate bacterial or other microorganisms. For instance, HINS light having a peak wavelength in the range of about 380 nanometers (nm) to about 420 nm (e.g., 405 nm) has been shown to inactivate certain microorganisms, such as certain gram-positive bacteria.

SUMMARY

Aspects and advantages of embodiments of the present disclosure will be set forth in part in the following description, or may be learned from the description, or may be learned through practice of the embodiments.

One example aspect of the present disclosure is directed to a method for controlling operation of a lighting system. The method includes operating the lighting system in a first mode to provide a first light output during a time period. The first light output can be a blend of HINS light and non-HINS light. The method includes determining, by one or more control devices, a dosage amount of HINS light provided during the time period. In addition, the method includes operating the lighting system in a second mode to provide a second light output based, at least in part, on the dosage amount. The second light output can be HINS light or a blend of HINS light and non-HINS light. Furthermore, spectral energy associated with the HINS light in the second light output can be greater than the spectral energy associated with the HINS light in the first light output.

Another example aspect of the present disclosure is directed to a lighting system. The lighting system includes one or more first light source configured to emit HINS light. The lighting system further includes one or more second light sources configured to emit at least non-HINS light. The lighting system includes one or more control devices. The one or more control devices are configured to operate the lighting system in a first mode to provide a first light output during a time period. The first light output includes a blend of the HINS light emitted from the one or more first light sources and non-HINS light emitted from the one or more second light sources. The one or more control devices are further configured to determine a dosage amount of HINS light provided during the time period. The one or more control devices are further configured to operate the lighting system in a second mode to provide a second light output based, at least in part, on the dosage amount. The second light output includes HINS light or a blend of HINS light and non-HINS light. Furthermore, the spectral energy associated with HINS light in the second light output is greater than spectral energy associated with the HINS light in the first light output.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which makes reference to the appended figures, in which.

DETAILED DESCRIPTION

Figure 1:
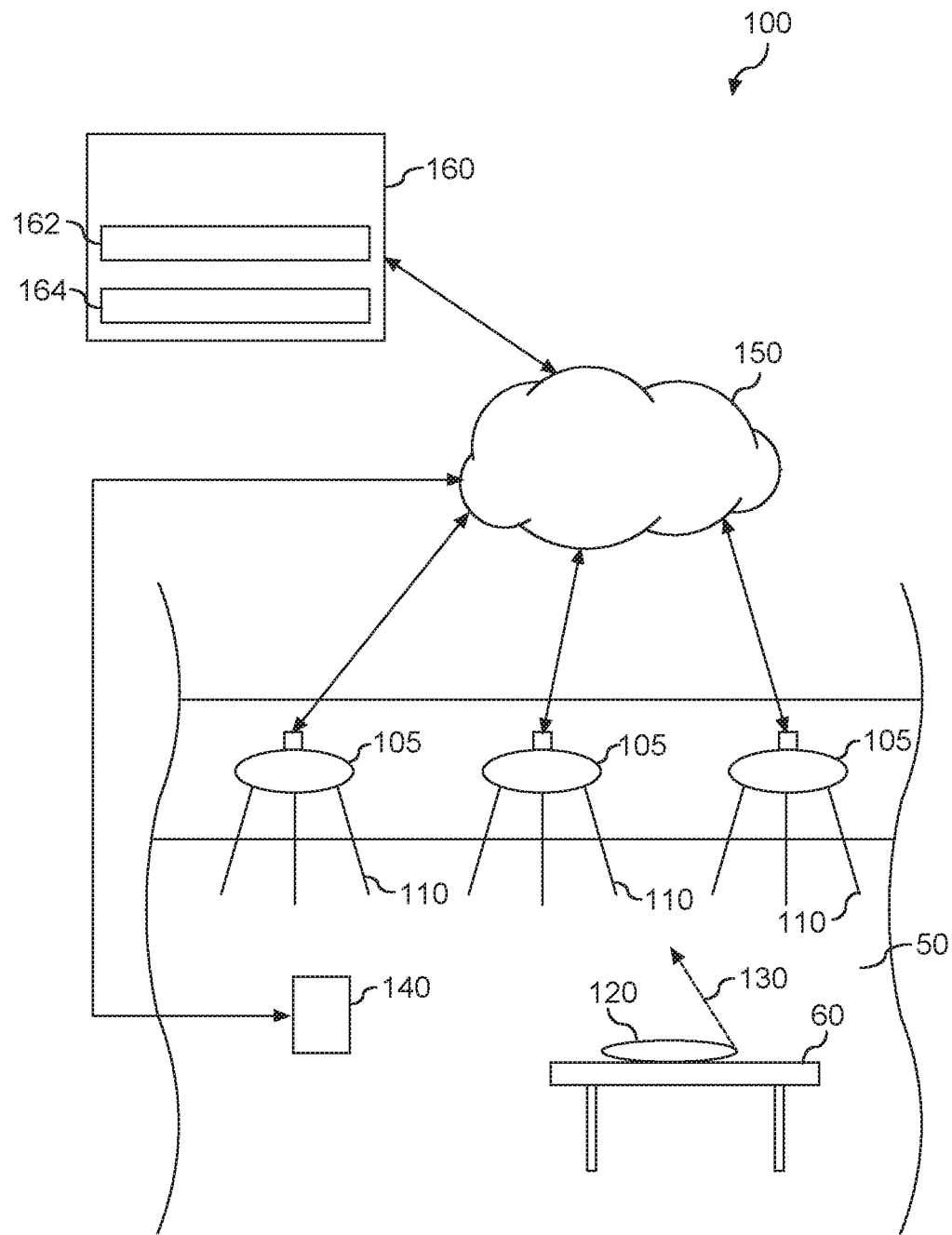
FIG. 1 depicts an overview of an example lighting system according to example embodiments of the present disclosure.

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Example aspects of the present disclosure are directed to lighting systems. In some implementations, the lighting system can include one or more first light sources and one or more second light sources. The one or more first light sources can be configured to emit HINS light. The one or more second light sources can be configured to emit at least non-HINS light. In some implementations, the one or more second light sources can be configured to emit HINS light and non-HINS light.

The lighting system can include one or more control devices configured to control operation of the lighting system. The one or more control devices can be configured to operate the lighting system in a first mode to provide a first light output during a time period. The first light output can include a blend of HINS light and non-HINS light. For instance, in some implementations, spectral energy associated with the HINS light in the first light output can be less than about 20% of a total spectral energy associated with the first light output.

In some implementations, the time period can correspond to a user-defined time period. For instance, a user can specify a duration of the time period via a user-device. In some implementations, the user device can be a mobile computing device (e.g., smartphone, tablet, etc.) that is communicatively coupled with the one or more control devices via a network.

The one or more control devices can be configured to determine a dosage amount of HINS light provided during the time period. In some implementations, the one or more control devices can be configured to determine a duration the lighting system provides the first light output during the time period. Furthermore, the one or more control devices can be configured to determine an intensity of the HINS light provided as part of the first light output during the time period. In this manner, the one or more control devices can determine the dosage amount based, at least in part, on the duration and the intensity of the HINS light provided as part of the first light output during the time period.

In some implementations, the one or more control devices can be configured to obtain data from a dosage feedback sensor associated with a space illuminated by the lighting system. For instance, the dosage feedback sensor can include one or more sensors configured to measure optical properties of the light illuminating the space. The optical properties can include, for instance, one or more wavelengths associated with the light and/or an intensity associated with the light. The one or more control devices can be configured to determine the dosage amount based, at least in part, on the data obtained from the dosage feedback sensor.

In some implementations, the one or more control devices can be configured to determine the dosage amount for a surface illuminated by the lighting system. For instance, in some implementations, the one or more control devices can be configured to determine the dosage amount as a function of a distance the one or more light sources are from the surface.

In some implementations, the one or more control devices can be configured to operate the lighting system in a second mode to provide a second light output. The second light output can be HINS light or a blend of HINS light and non-HINS light. Furthermore, spectral energy associated with HINS light in the second light output can be greater than spectral energy associated with HINS light in the first light output. For instance, in some implementations, the spectral energy associated with HINS light in the second light output can be greater than about 20% of a total spectral energy associated with the second light output.

In some implementations, the one or more control devices can be configured to determine a duration to provide the second light output based, at least in part on the dosage amount. For instance, the one or more control devices can be configured to compare the dosage amount to a threshold dosage amount. The threshold dosage amount can correspond to an amount of HINS light to be provided during the time period. In some implementations, the threshold dosage amount can be specified by a user. For instance, a user can enter the threshold dosage amount via a graphical user interface displayed on a mobile computing device that is communicatively coupled with the one or more control devices.

In some implementations, the one or more control devices can be configured to determine the duration to provide the second light output based, at least in part, on a difference between the dosage amount and the threshold dosage amount. For instance, the one or more control devices can be configured to determine the duration to provide the second light output as a function of intensity of the HINS light in the second light output and the difference between the dosage amount and the threshold dosage amount.

In some implementations, the one or more control devices can be configured to switch operation of the lighting system between the first mode and the second mode based, at least in part, on data obtained from an occupancy sensor associated with the space illuminated by the lighting system. When the data obtained from the occupancy sensor indicates presence of one or more persons within the space, the one or more control devices can be configured to control operation of the lighting system such that the lighting system operates in the first mode. Conversely, the one or more control devices can control operation of the lighting system such that the lighting system operates in the second mode when the data from the occupancy sensor indicate one or more persons are not present within the space.

In some implementations, operation of the lighting system can switch between the first mode and the second mode as data obtained from the occupancy sensor indicates one or more users entering and exiting the space illuminated by the lighting system. In such implementations, the one or more control devices can be configured to determine a total dosage amount associated with the first light output and the second light output during the time period. Furthermore, the one or more control devices can be configured to determine a difference between the total dosage amount and a threshold dosage amount of HINS light needed for antimicrobial purposes. As such, the one or more control devices can be further configured to operate the lighting system in the second mode to provide an additional dosage of HINS light needed such that the space is illuminated with at least the threshold dosage amount of HINS light needed for antimicrobial purposes.

The lighting system of the present disclosure can provide numerous technical benefits. For instance, as discussed above, the one or more control devices can be configured to determine a difference between a dosage amount of HINS light provided during a time period and a threshold dosage amount. Furthermore, the one or more control devices can be configured to operate the lighting system in the second mode to dose the space with an additional amount of HINS light needed such that the space is illuminated with at least the threshold dosage amount of HINS light. In this manner, operation of the lighting system can be improved such that spaces illuminated by the lighting system can be dosed with a sufficient amount of HINS light needed for antimicrobial purposes.

As used herein, a lighting system can include, but is not limited to, one or more of a lighting circuit, light engine, one or more luminaires, one or more lighting fixtures, one or more lighting units, a plurality of lighting devices arranged in an environment, a combination of any of the foregoing, etc. HINS light refers to light having at least one peak wavelength in the range of about 380 nanometers (nm) to about 420 nm, such as about 400 nm to about 420 nm, such as about 405 nm. Non-HINS light refers to light in the visible spectrum, but outside the HINS range of 380 nm to 405 nm. As used herein, the use of the term "about" in conjunction with a numerical value refers to within 5% of the stated numerical value.

Referring now to the FIGS, FIG. 1 depicts a lighting system 100 according to example embodiments of the present disclosure. The lighting system 100 can include a plurality of lighting fixtures 105. Each of the lighting fixtures 105 can be configured to provide light 110 to illuminate a space 50 and/or a surface 60. One or more of the lighting fixtures 105 can include one or more HINS light sources (e.g., HINS LEDs). The HINS light sources can be configured to emit HINS light (e.g., as all or as a part of light 110) into space 50 and/or onto surface 60 for various purposes, such as antimicrobial purposes. Optionally, the lighting fixtures 105 can include one or more non-HINS light sources. The HINS light can be combined with other wavelengths of light emitted by the non-HINS light sources, for instance through electroluminescence or photoluminescence, to create visible white light or other desired effects.

As shown, the lighting system 100 can include a dosage feedback sensor 120. The dosage feedback sensor 120 can be a device that is placed on the surface 60 illuminated by the light 110. The dosage feedback sensor 120 can include optical sensors and/or other measurement devices configured to measure characteristics of the light 110, including HINS light, emitted onto the surface 60. Furthermore, although the dosage feedback sensor 120 of FIG. 1 is configured with a circular shape/form factor, it should be appreciated that the dosage feedback sensor can take any suitable shape or form factor without deviation from the scope of the present disclosure.

In some implementations, the lighting system 100 can include an occupancy sensor 140 disposed within the space 50 illuminated by the lighting system 100. The occupancy sensor 140 can include any suitable device configured to obtain data indicative of whether one or more persons are present within the space 50. For instance, the occupancy sensor 140 can include one or more motion detectors (e.g., PIR sensors) positioned at different locations within the space 50. In this manner, the one or more motion detectors can obtain data indicative of whether a person is present within the space 50.

As shown, the lighting system 100 can include one or more control devices 160. In some implementations, the one or more control devices 160 can be onboard the plurality of lighting fixtures 105. In alternative implementations, the one or more control devices 160 can be remote relative to the lighting fixtures 105 and communicatively coupled to the plurality of lighting fixture 105 via a network 150 (e.g., wired or wireless).

In some implementations, the one or more control devices 160 can be communicatively coupled to the dosage feedback sensor 120 and the occupancy sensor 140 via the network 150. In this manner, the one or more control devices 160 can obtain data 130 from the dosage feedback sensor 120 and data from the occupancy sensor 140. The one or more control devices 160 can include one or more processors 162 and one or more memory devices 164. As such, the one or more control devices 160 can process the data 130 obtained from the dosage feedback sensor 120, the data obtained from the occupancy sensor 140, or both. As will be discussed below in more detail, the one or more control devices 160 can be configured to control operation of the lighting system 100 based, at least in part, on the data 130 obtained from the dosage feedback sensor 120, the data obtained from the occupancy sensor 140, or both.

Figure 2:
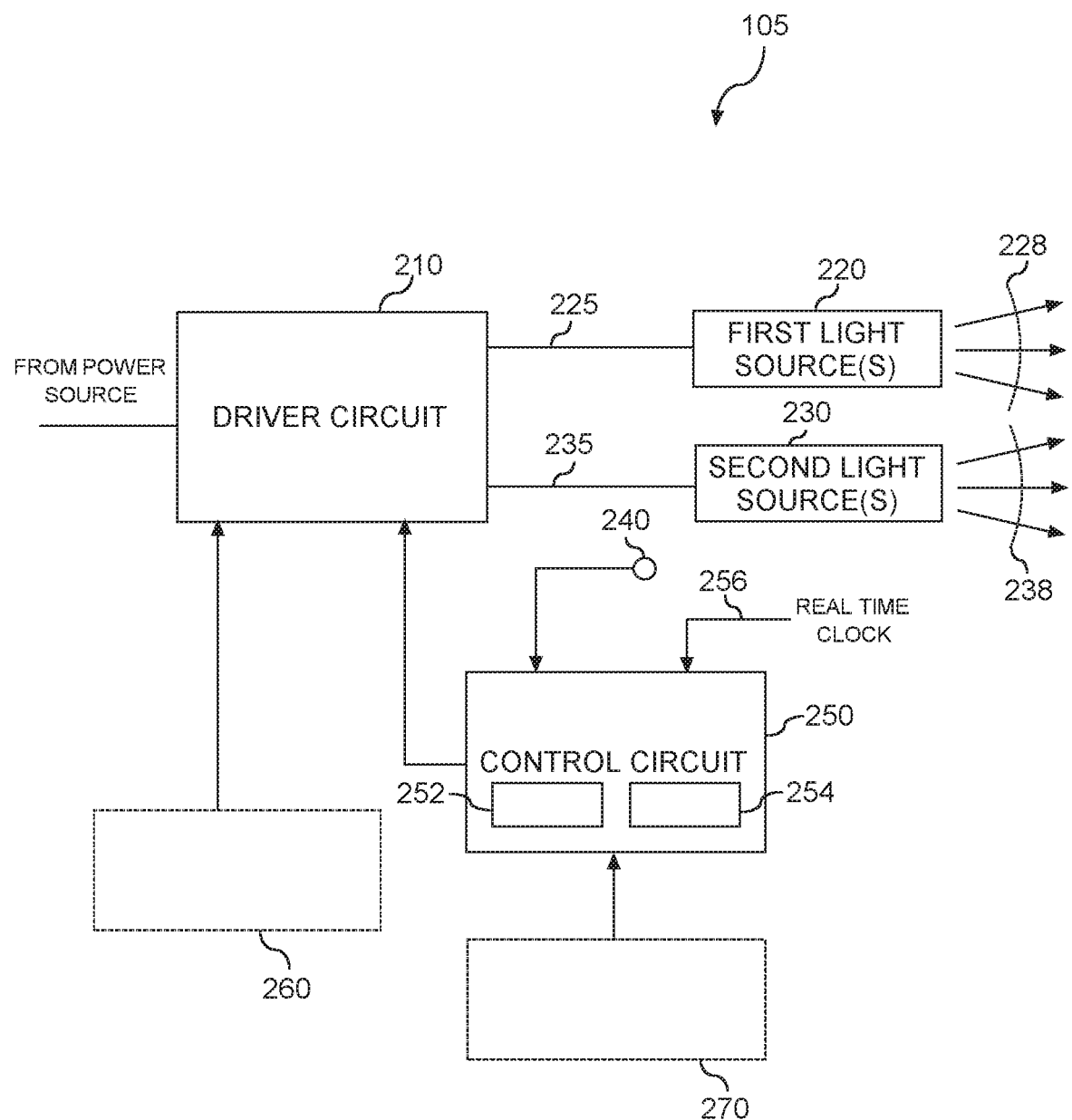
FIG. 2 depicts components of an example lighting fixture of a lighting system according to example embodiments of the present disclosure.

FIG. 2 depicts a block diagram of example components of a lighting fixture 105 of the lighting system 100 (FIG. 1) according to example embodiments of the present disclosure. The components shown in FIG. 2 are illustrated as part of the same lighting fixture 105. However, those of ordinary skill in the art, using the disclosures provided herein, will understand that one or more of the components can be distributed across multiple platforms, lighting fixtures, systems, etc.

As shown, the lighting fixture 105 can include an LED driver circuit 210, a control circuit 250, one or more first light sources 220 configured to emit HINS light, and one or more second light sources 230 configured to emit at least non-HINS light. The one or more first light sources 220 and the one or more second light sources 230 can be arranged in any suitable manner.

Optionally, as shown in FIG. 2, the one or more first light sources 220 can emit light through a first optic 228 so as to provide light associated with a first distribution. The one or more second light sources 230 can emit light through a second optic 238 so as to provide light associated with a second distribution. The first distribution can be different from the second distribution. In this way, the distribution of HINS light relative to non-HINS light in a lighting system can be more specifically controlled, for instance, to illuminate specific surfaces for antimicrobial purposes. The non-HINS light sources can provide light using a distribution to provide general illumination for the space 50 and/or surface 60.

The driver circuit 210 can be, for instance, any suitable driver circuit configured to convert an input power (e.g., an input AC or DC power) to a suitable driver output (e.g. driver current) for powering the one or more first light sources 220 and the one or more second light sources 230. In some embodiments, the driver circuit 210 can be a dimmable driver circuit. The driver circuit 210 is illustrated as a multichannel driver circuit configured to power the one or more first light sources 220 over a first channel 225 and to power the one or more second light sources 230 over a second channel 235. Other suitable arrangements can be used to provide power to the one or more first light sources 220 and the one or more second light sources 230 without deviating from the scope of the present disclosure. For instance, independent driver circuits can be used to power the one or more first light sources 220 and the one or more second light sources 230. In some implementations, the driver circuit 210 can be implemented on the same circuit board as the one or more first light sources 220 and/or the one or more second light sources 230.

In some implementations, the dimmable driver circuit 210 can include various components, such as switching elements (e.g. transistors) that are controlled to provide a suitable driver output. For instance, in some implementations, the driver circuit 210 can include one or more transistors. Gate timing commands can be provided to the one or more transistors to convert the input power to a suitable driver output using pulse width modulation techniques. In some implementations, the dimmable driver circuit 210 can be a line dimming driver, such as a phase-cut dimmable driver, Triac dimmer, trailing edge dimmer, or other line dimming driver. The driver output can be adjusted using the line dimming driver by controlling the input power to the dimmable driver circuit 210.

In some implementations, an interface 260 can be provided at the driver circuit 210 for receiving a dimming control signal used to control the driver output. The interface 260 can include one or more components for communicating a dimming control signal to the driver circuit 210. For example, the interface 260 can include one or more circuits, terminals, pins, contacts, conductors, or other components for communicating a dimming control signal to the driver circuit 210.

The dimming control signal can be provided from an external circuit, such as an external dimming circuit or external control device. The external circuit can include one or more devices, such as a smart dimming interface, a potentiometer, a Zener diode, or other device. In some implementations, the dimming control signal can be received from the control circuit 250. In some implementations, the dimming control signal can be a 0V to 10V dimming control signal. The dimming control signal can be implemented using other suitable protocols, such as a DALI protocol, or a DMX protocol.

In some implementations, the dimming control signal can be received from a remote device over a wireless communication medium or other communication medium. Example communication technologies can include, for instance, Bluetooth low energy, Bluetooth mesh networking, near-field communication, Thread, TLS (Transport Layer Security), Wi-Fi (e.g., IEEE, 802.11), Wi-Fi Direct (for peer-to-peer communication), Z-Wave, Zigbee, Halow, cellular communication, LTE, low-power wide area networking, VSAT, Ethernet, MoCA (Multimedia over Coax Alliance), PLC (Power-line communication), DLT (digital line transmission), etc. Other suitable wired and/or wireless communication technologies can be used without deviating from the scope of the present disclosure.

The control circuit 250 can be configured to control the delivery of power to the one or more first light sources 220 and the one or more second light sources 230 from the driver circuit 210 to provide various lighting effects, such as for providing a combined light output from the one or more first light sources 220 and the one or more second light sources 230 of a desired color and/or color temperature or other lighting effect. For example, the control circuit 250 can independently control the driver output provided over the first channel 225 and the second channel 235 so that the light output of the one or more first light sources 220 and the one or more second light sources 230 can be independently controlled to achieve desired lighting effects.

As illustrated, the control circuit 250 can include one or more processors 252 and one or more memory devices 254. The one or more memory devices 254 can store computer-readable instructions that, when executed by the one or more processors 252, cause the one or more processors 252 to provide control functionality according to example aspects of the present disclosure. For instance, the one or more memory devices 254 can store computer-readable instructions that, when executed by the one or more processors 252, cause the control circuit 250 to control the light output of the lighting fixture 105 according to one or more control schemes. The control schemes can be pre-programmed into the memory devices 254 or may be programmed by a user from time-to-time in one or memory devices 254 using a suitable user interface.

The control circuit 250 can be implemented on the same circuit board as the driver circuit 210 or can be located remote from the driver circuit 210 and/or the lighting fixture 105. In some implementations, the control circuit 250 can control the driver circuit 210 over a suitable communication medium, such as a wired or wireless communication medium.

In some implementations, the control circuit 250 can include an interface 270 for receiving a lighting control signal or other control signal. The interface 270 can include one or more components for communicating the lighting control signal to the control circuit 250. For example, the interface 270 can include one or more circuits, terminals, pins, contacts, conductors, transmitters, receivers, transceivers, or other components for communicating the lighting control signal.

In some implementations, the interface 270 can receive a lighting control signal over a wireless communication interface. Example communication technologies can include, for instance, Bluetooth low energy, Bluetooth mesh networking, near-field communication, Thread, TLS (Transport Layer Security), Wi-Fi (e.g., IEEE, 802.11), Wi-Fi Direct (for peer-to-peer communication), Z-Wave, Zigbee, Halow, cellular communication, LTE, low-power wide area networking, VSAT, Ethernet, MoCA (Multimedia over Coax Alliance), PLC (Power-line communication), DLT (digital line transmission), etc. Other suitable wired and/or wireless communication technologies can be used without deviating from the scope of the present disclosure.

The control circuit 250 and/or lighting control signal can specify control of the lighting fixture 105 (e.g., the amount of driver output to provide to the one or more first light sources 220 and the one or more second light sources 230) based on various parameters and/or control schemes to provide smart control functionality. For example, the control circuit 250 can receive signals from one or more sensors 240 (e.g., optical sensors, motion sensors, etc.) and control light output of the one or more first light sources 220 and the one or more second light sources 230 so that the light output of the lighting fixture 105 meets desired requirements (e.g., a specified amount of HINS light for antimicrobial purposes).

As another example, the control circuit 250 can adjust the combined light output of the lighting fixture 105 according to a defined light profile based at least in part on a signal 256 associated with a real time clock. The defined light profile can specify an adjustment in the color temperature and/or other characteristics of the collective light output over time based at least in part on entrainment of a circadian rhythm of a living organism exposed to the light output and/or based on user settings or preferences. For instance, in some implementations, the defined light profile can be defined at least in part on a natural day/night cycle.

As another example, the color temperature or other characteristics of the combined light can be controlled based on data indicative of user preferences. For instance, if a user prefers a more bluish color temperature, the one or more first light sources 220 and the one or more second light sources 230 can be controlled to provide a combined light output with a more bluish color temperature. If a user prefers a more reddish color temperature, the one or more first light sources 220 and the one or more second light sources 230 can be controlled to provide a combined light output with a more reddish color temperature. The data indicative of user preferences can be obtained or accessed from, for instance, user devices (e.g., smartphones, tablets, fitness trackers) carried by a user and communicated to the lighting system 100 over a suitable communication medium or media.

Figure 3:
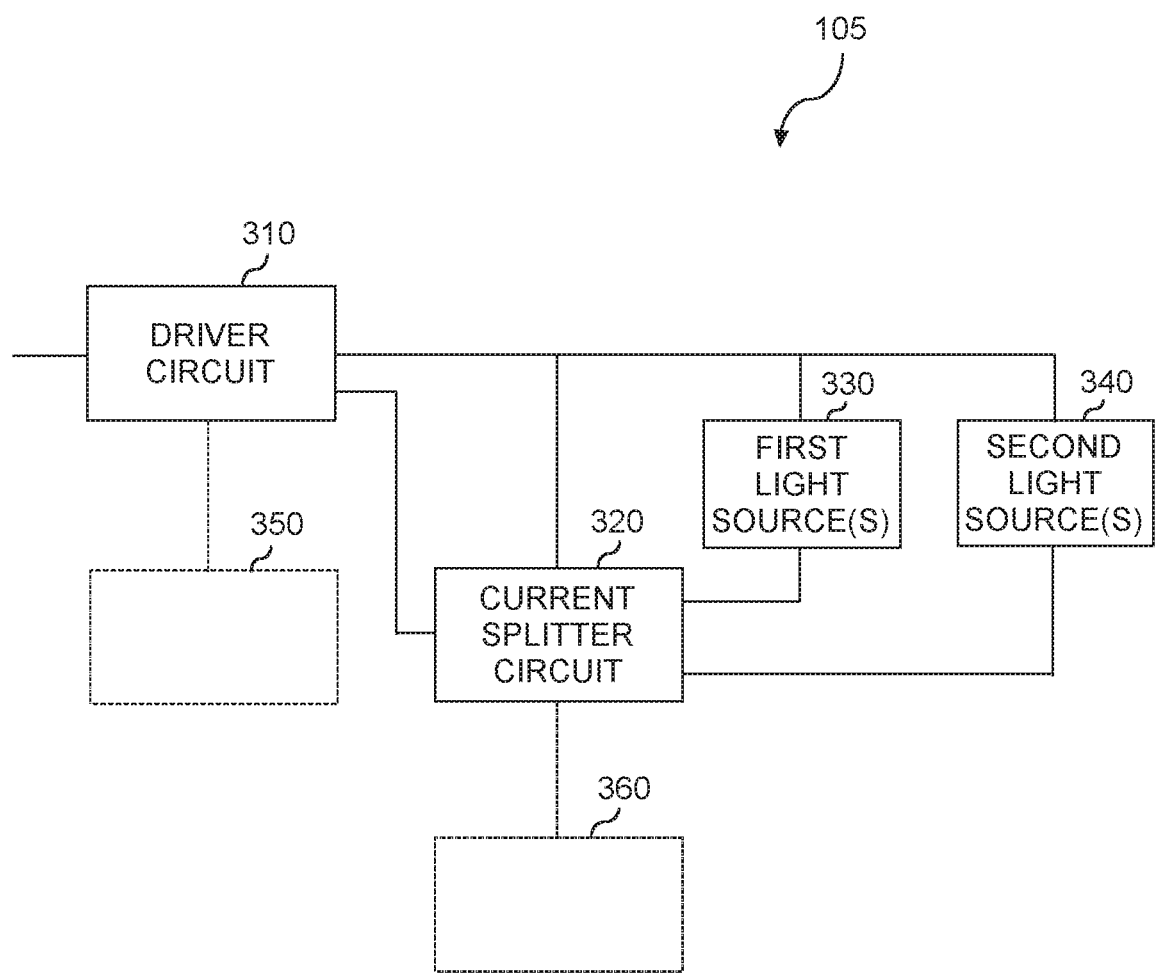
FIG. 3 depicts components of an example lighting fixture of a lighting system according to example embodiments of the present disclosure.

Referring now to FIG. 3, a block diagram of another embodiment of the lighting fixture 105 is provided according to example embodiments of the present disclosure. As shown, the lighting fixture 105 can include an LED driver circuit 310, a current splitter circuit 320, one or more first light sources 330 and one or more second light sources 340. The one or more first light sources 330 and one or more second light sources 340 can be arranged in any suitable manner. The one or more first light sources 330 can be configured to emit HINS light. The one or more second light sources 340 can be configured to emit at least non-HINS light. In some implementations, the one or more second light sources 340 can be configured to emit a blend of HINS light and non-HINS light.

The LED driver circuit 310 can be configured to receive an input power, such as an input AC power or an input DC power, and can convert the input power to a suitable driver output (e.g. driver current) for powering the plurality of LED arrays. In some embodiments, the driver circuit 310 can be a dimmable driver circuit. The dimmable driver circuit 310 can include various components, such as switching elements (e.g. transistors) that are controlled to provide a suitable driver output. For instance, in one embodiment, the driver circuit 310 can include one or more transistors. Gate timing commands can be provided to the one or more transistors to convert the input power to a suitable driver output using pulse width modulation techniques. In some example embodiments, the dimmable driver circuit 310 can be a line dimming driver, such as a phase-cut dimmable driver, Triac dimmer, trailing edge dimmer, or other line dimming driver. The driver output can be adjusted using the line dimming driver by controlling the input power to the dimmable driver circuit.

Alternatively or additionally, a first interface 350 can be provided at the dimmable driver circuit 310 for receiving a dimming control signal used to control the driver output. The first interface 350 can include one or more components for communicating the dimming control signal to the driver circuit 310. For example, the first interface 350 can include one or more circuits, terminals, pins, contacts, conductors, receivers, transmitters, transceivers, or other components for communicating the dimming control signal to the driver circuit 310.

The dimming control signal can be provided from an external circuit, such as an external dimming circuit. The external circuit can include one or more devices, such as a smart dimming interface, a potentiometer, a Zener diode, or other device. In one example implementation, the dimming control signal can be a 0V to 10V dimming control signal, depending on the output of the external circuit. For instance, if a user manually adjusts a dimmer, the dimming control signal can be adjusted from, for instance, 0V to 5V. The dimming control signal can be implemented using other suitable protocols, such as a digital addressable lighting interface (DALI) lighting control signal, digital multiplex (DMX) lighting control signal, or other suitable protocol.

In some implementations, the dimming control signal can be received from a remote device over a wireless communication medium or other communication medium. Example communication technologies can include, for instance, Bluetooth low energy, Bluetooth mesh networking, near-field communication, Thread, TLS (Transport Layer Security), Wi-Fi (e.g., IEEE, 802.11), Wi-Fi Direct (for peer-to-peer communication), Z-Wave, Zigbee, Halow, cellular communication, LTE, low-power wide area networking, VSAT, Ethernet, MoCA (Multimedia over Coax Alliance), PLC (Power-line communication), DLT (digital line transmission), etc. Other suitable wired and/or wireless communication technologies can be used without deviating from the scope of the present disclosure.

The driver circuit 310 can be configured to adjust the driver output based, at least in part, on the dimming control signal. As a result, the light output of the one or more first light sources 330 and the one or more second light sources 340 can be simultaneously adjusted (e.g. dimmed) by varying the dimming control signal.

As illustrated in FIG. 3, the driver output can be provided to a current splitter circuit 320. The current splitter circuit 320 can be configured to split the driver output into a first current for powering the one or more first light sources 330 and a second current for powering the one or more second light sources 340. In this way, the current splitter circuit 320 can be used to adjust the light output of the one or more first light sources 330 relative to the light output of the one or more second light sources 340. The current splitter circuit 320 can be configured to control the current ratio of the first current provided to the one or more first light sources 330 relative to the second current provided to the one or more second light sources 340 based on a lighting control signal.

In some implementations, the current splitter circuit 320 can include one or more switching elements (e.g., transistors) used to control a current provided to the one or more first light sources 330. The current splitter circuit 320 can include one or more switching elements (e.g., transistor) used to a control a current provided to the one or more second light sources 340. The switching elements can be controlled using pulse width modulation to split the current from the driver circuit 310 among the one or more first light sources 330 and the one or more second light sources 340 according to a lighting control signal.

More particularly, a second interface 360 provided at the current splitter circuit 320 can receive a lighting control signal (e.g., variable reference signal). The second interface 360 can include one or more components for communicating the variable reference signal to the current splitter circuit 320. For example, the second interface 360 can include one or more circuits, terminals, pins, contacts, conductors, receivers, transmitters, transceivers, or other components for communicating a variable reference signal to the current splitter circuit 320.

The control signal can be provided from an external circuit, such as an external dimming circuit, over for instance, a network. The external circuit can include one or more devices, such as a smart dimming interface, remote control, control interface, a potentiometer, a Zener diode, or other device. The control signal can be a 0V to 10V lighting control signal, depending on the output of the external circuit. The control signal can be implemented using other suitable protocols, such as a DALI protocol, or a DMX protocol.

In some implementations, the lighting control signal can be received from a remote device over a wireless communication medium or other communication medium. Example communication technologies can include, for instance, Bluetooth low energy, Bluetooth mesh networking, near-field communication, Thread, TLS (Transport Layer Security), Wi-Fi (e.g., IEEE, 802.11), Wi-Fi Direct (for peer-to-peer communication), Z-Wave, Zigbee, Halow, cellular communication, LTE, low-power wide area networking, VSAT, Ethernet, MoCA (Multimedia over Coax Alliance), PLC (Power-line communication), DLT (digital line transmission), etc. Other suitable wired and/or wireless communication technologies can be used without deviating from the scope of the present disclosure.

The current splitter circuit 320 can include one or more control devices (e.g. a microprocessor, a microcontroller, logic device, etc.) and one or more switching elements (e.g. transistors) in line with each of the one or more first light sources 330 and the one or more second light sources 340. The control device(s) can control the amount of current provided to the one or more first light sources 330 and the one or more second light sources 340 by controlling the switching elements. The switching elements used to control the amount of current provided to the one or more first light sources 330 and the one or more second light sources 340 can be either on the low voltage side of the LED arrays or the high voltage side of the one or more first light sources 330 and the one or more second light sources 340.

In particular aspects, the control device(s) can control the current provided to the one or more first light sources 330 and the one or more second light sources 340 according to a current ratio control curve based on the variable reference signal. The current ratio control curve can be stored in firmware or stored in a memory accessible by the control device(s). The current ratio control curve can specify the current ratio of the first current provided to the one or more first light sources 330 and the one or more second light sources 340 as a function of at least the control signal.

The control device(s) of the current splitter circuit 320 can specify control of the lighting fixture 105 (e.g., the amount of driver output to provide to the one or more first light sources 330 and the one or more second light sources 340) based on various parameters and/or control schemes to provide smart control functionality. For example, the current splitter circuit 320 can receive signals from one or more sensors (e.g., optical sensors, motion sensors, etc.) and can control light output of the one or more first light sources 330 and the one or more second light sources 340 so that the light output of the lighting system 300 meets desired requirements (e.g., a specified amount of HINS light for antimicrobial purposes).

As another example, the current splitter circuit 320 can adjust the combined light output of the lighting fixture 105 according to a defined light profile based at least in part on a signal associated with a real time clock. The defined light profile can specify an adjustment in the color temperature of the collective light output over time based at least in part on entrainment of a circadian rhythm of a living organism exposed to the light output and/or based on user settings or preferences. For instance, in some embodiments, the defined light profile can be defined at least in part on a natural day/night cycle. Other suitable defined light profiles can be used without deviating from the scope of the present disclosure.

As yet another example, the color temperature or other characteristics of the combined light can be controlled based on data indicative of user preferences. For instance, if a user prefers a more bluish color temperature, the current splitter circuit 320 can be controlled to provide a combined light output with a more bluish color temperature. If a user prefers a more reddish color temperature, the current splitter circuit 320 can be controlled to provide a combined light output with a more reddish color temperature. The data indicative of user preferences can be obtained or accessed from, for instance, user devices (e.g., smartphones, tablets, fitness trackers) carried by a user and communicated to a lighting system over a suitable communication medium or media.

Figure 4:
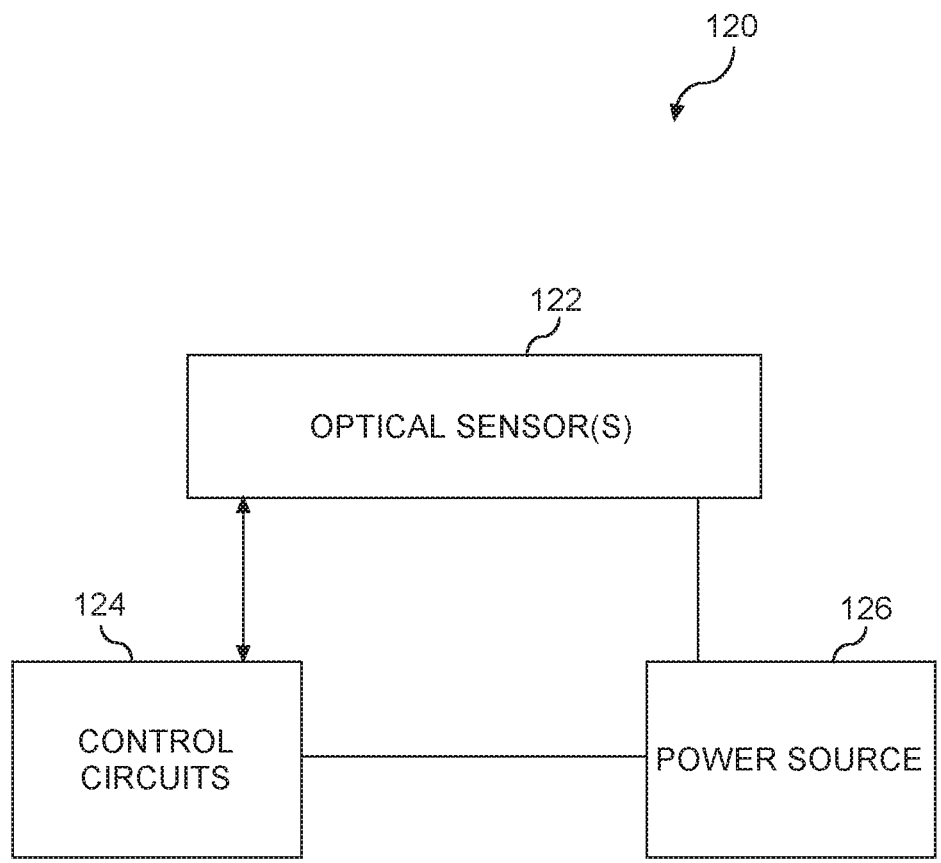
FIG. 4 depicts an example dosage feedback sensor according to example embodiments of the present disclosure.

Referring now to FIG. 4, components of an example dosage feedback sensor 120 are provided according to present disclosure. As shown, the dosage feedback sensor 120 can include one or more optical sensors 122, one or more control circuits 124, and a power source 126. The one or more optical sensors 122 can be configured to measure optical properties of light 110 (FIG. 1) emitted onto the dosage feedback sensor 120 and to generate one or more signals indicative of optical properties associated with the light 110. The optical properties can include, for instance, one or more wavelengths associated with the light and/or an intensity associated with the light. The one or more optical sensors 122 can include, for instance, a spectrometer, one or more photodiodes, devices for converting light into electrical signals, other sensors, or combination of the foregoing.

The one or more signals indicative of the optical properties of the light can be provided to the one or more control circuits 124 of the dosage feedback sensor 120. The one or more control circuits 124 can process the one or more signals and provide the data 130 (FIG. 1) indicative of the one or more optical properties to the one or more control devices 160 (FIG. 1) via the network 150 (FIG. 1).

The power source 126 of the dosage feedback sensor 120 can be any suitable power source for powering the various components of the dosage feedback sensor 120. In some implementations, the power source 126 can be a battery power source, solar power source, or other suitable power source so that the dosage feedback sensor 120 does not need to be hard wired to a power source for operation.

Figure 5:
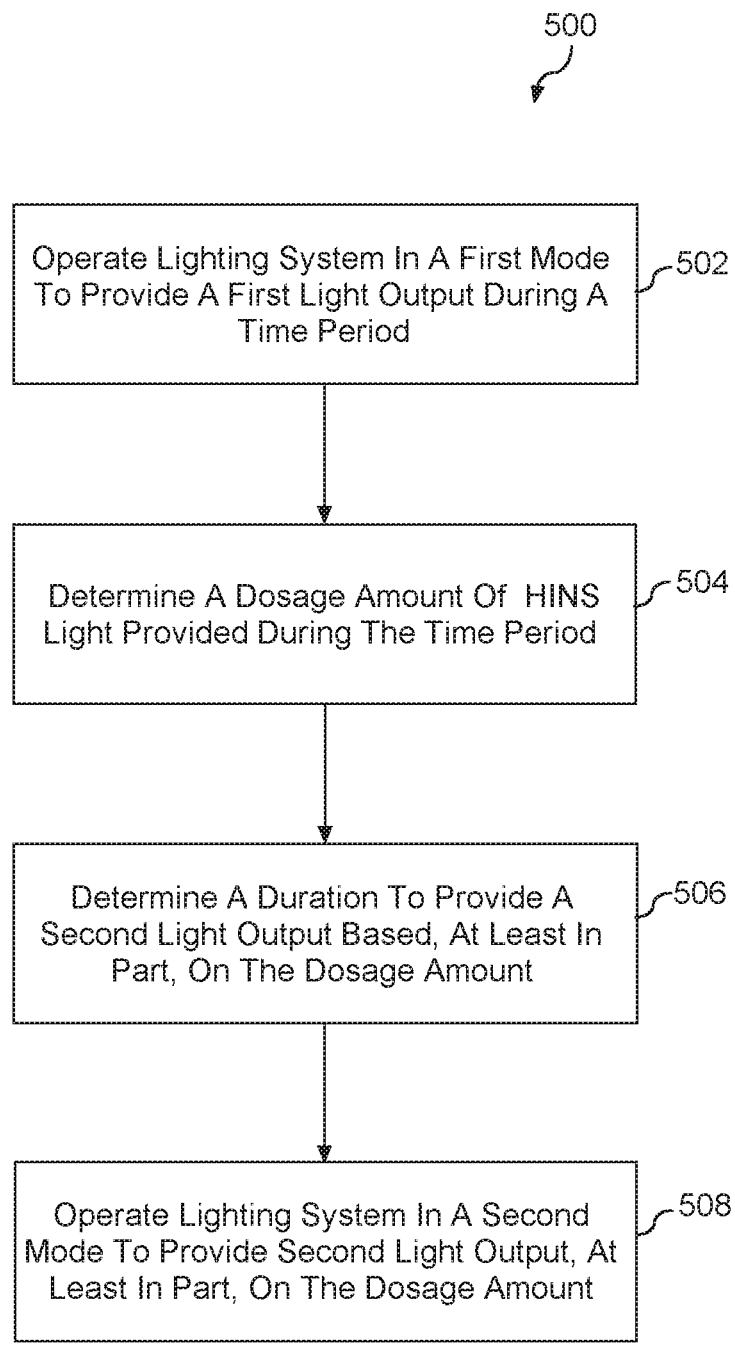
FIG. 5 depicts a flow diagram of a method for controlling operation of a lighting system according to example embodiments of the present disclosure.

Referring now to FIG. 5, a flow diagram of one example method (500) for controlling operation of a lighting system is provided according to example embodiments of the present disclosure. The method 500 can be implemented by, for instance, the one or more control devices 160 of the lighting system 100 discussed above with reference to FIG. 1. FIG. 5 depicts steps performed in a particular order for purposes of illustration and discussion. Those of ordinary skill in the art, using the disclosures provided herein, will understand that various steps of any of the methods disclosed herein can be omitted, rearranged, expanded, adapted, and/or modified in various ways without deviating from the scope of the present disclosure.

At (502), the method 500 can include operating the lighting system in a first mode to provide a first light output during a time period. In some implementations, the first light output can be a blend of HINS light and non-HINS light. Furthermore, in some implementations, the time period can correspond to a user-defined time period. For instance, in some implementations, the user-defined time period can be entered via a user device that is in communication with one or more control devices of the lighting system. Examples of user devices can include, without limitation, a mobile computing device (e.g., smartphone, tablet, etc.).

Figure 6:
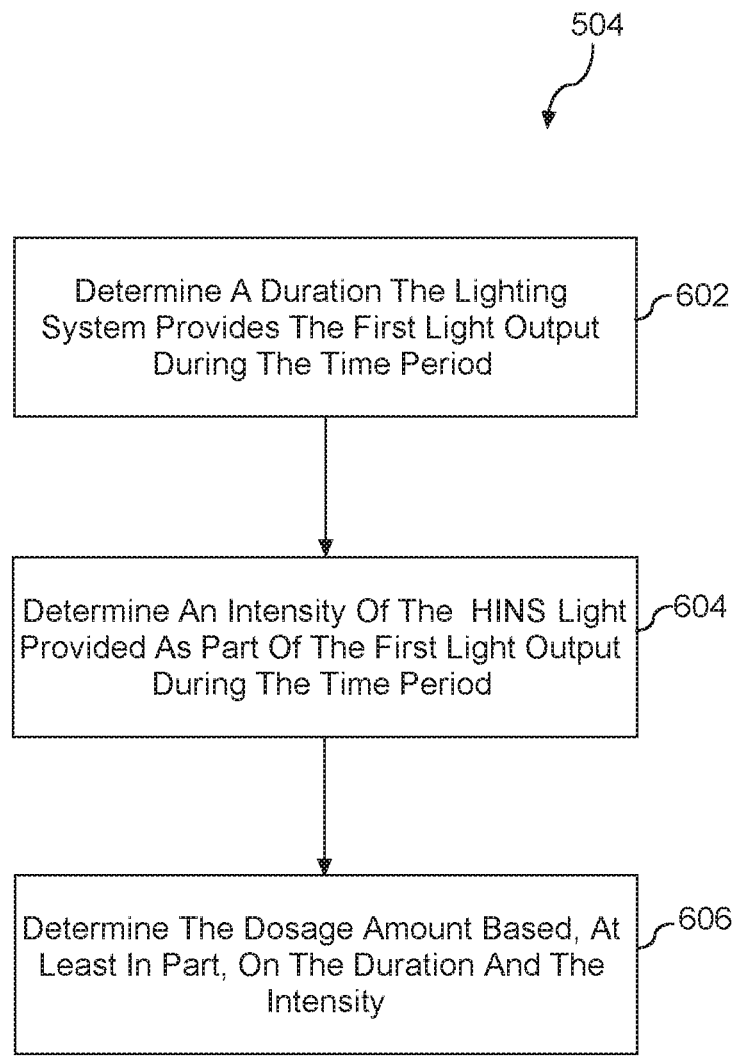
FIG. 6 depicts a flow diagram of a method for determining a dosage amount of HINS light provided by a lighting system during a time period according to example embodiments of the present disclosure.

At (504), the method 500 can include determining, by one or more control devices, a dosage amount of HINS light provided during the time period. Referring briefly now to FIG. 6, a flow diagram of a method for determining the dosage amount at (504) is provided according to example embodiments of the present disclosure. At (602), the method for determining the dosage amount at (504) can include determining, by the one or more control devices, a duration the lighting system provides the first light output during the time period. At (604), the method for determining the dosage amount at (504) can include determining, by the one or more control devices, an intensity of the HINS light provided as part of the first light output during the time period. At (606), the method for determining the dosage amount at (504) can include determining, by the one or more control devices, the dosage amount based, at least in part, on the duration determined at (602) and the intensity determined at (604).

Figure 7:
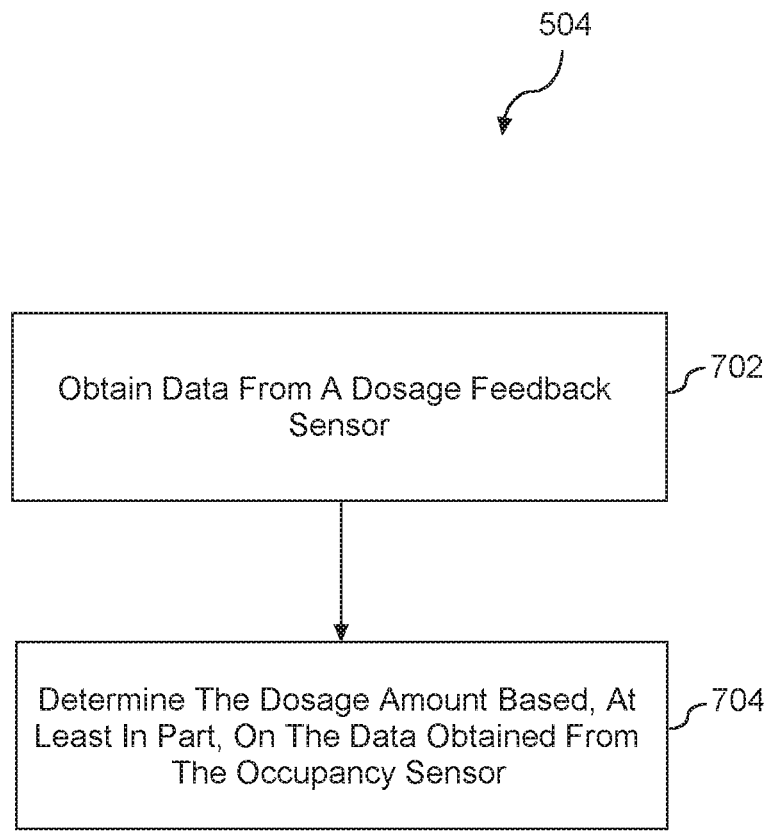
FIG. 7 depicts a flow diagram of another method for determining a dosage amount of HINS light provided by a lighting system during a time period according to example embodiments of the present disclosure.

Referring briefly now to FIG. 7, a flow diagram of another method for determining the dosage amount at (504) is provided according to example embodiments of the present disclosure. At (702), the method for determining the dosage amount at (504) can include obtaining, by the one or more control devices, data from a dosage feedback sensor. At (704), the method for determining the dosage amount at (504) can further includes determining, by the one or more control devices, the dosage amount based, at least in part, on the data obtained from the dosage feedback sensor at (702).

Figure 8:
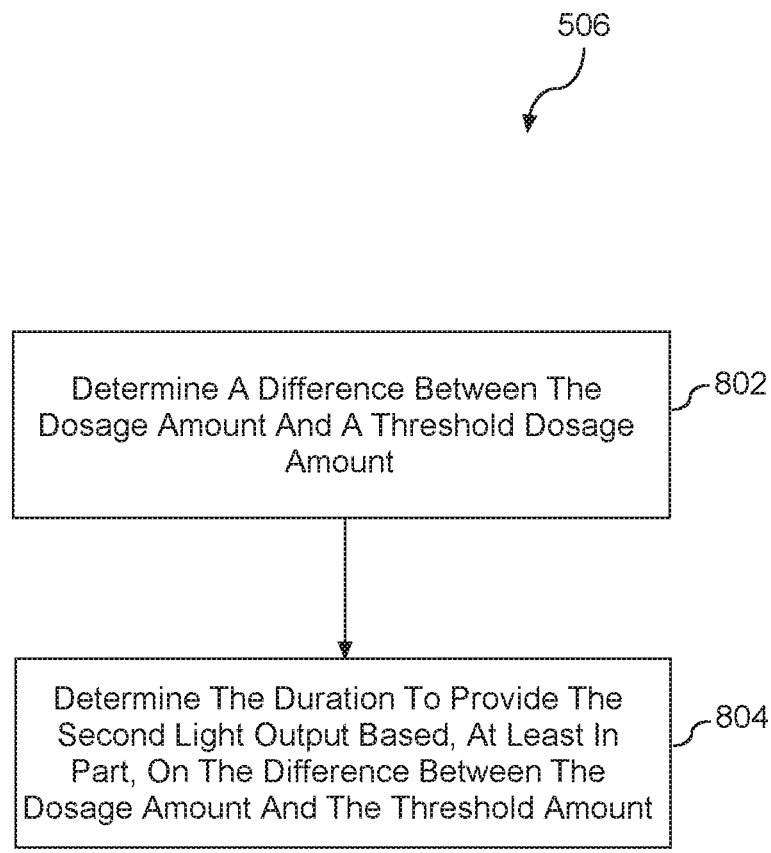
FIG. 8 depicts a flow diagram of a method for determining a duration to provide a second light output according to example embodiments of the present disclosure.

Referring again to FIG. 5, the method 500 for controlling operation of the lighting system can include, at (506), determining a duration to provide a second light output based, at least in part on the dosage amount. Referring briefly now to FIG. 8, a flow diagram of a method for determining the duration to provide the second light output is provided according to example embodiments of the present disclosure. At (802), the method for determining the duration to provide the second light output at (506) includes determining, by the one or more control devices, a difference between the dosage amount determined at (506) and a threshold dosage amount. For instance, the one or more control devices are configured to compare the dosage amount to the threshold dosage amount to determine whether the dosage amount is different (e.g., less than or greater than) the threshold dosage amount. In this manner, the one or more control devices can determine the difference (e.g., delta) between the dosage amount and the threshold dosage amount.

At (804), the method for determining the duration to provide the second light output at (506) can include determining, by the one or more control devices, the duration to provide the second light output based, at least in part, on the difference between the dosage amount and the threshold amount. For example, if the one or more control devices determine the dosage amount is less than the threshold dosage amount, the one or more control devices can be configured to determine the duration to provide the second light output corresponds to an amount of time needed such that the space is dosed with the threshold dosage amount of HINS light.

Figure 9:
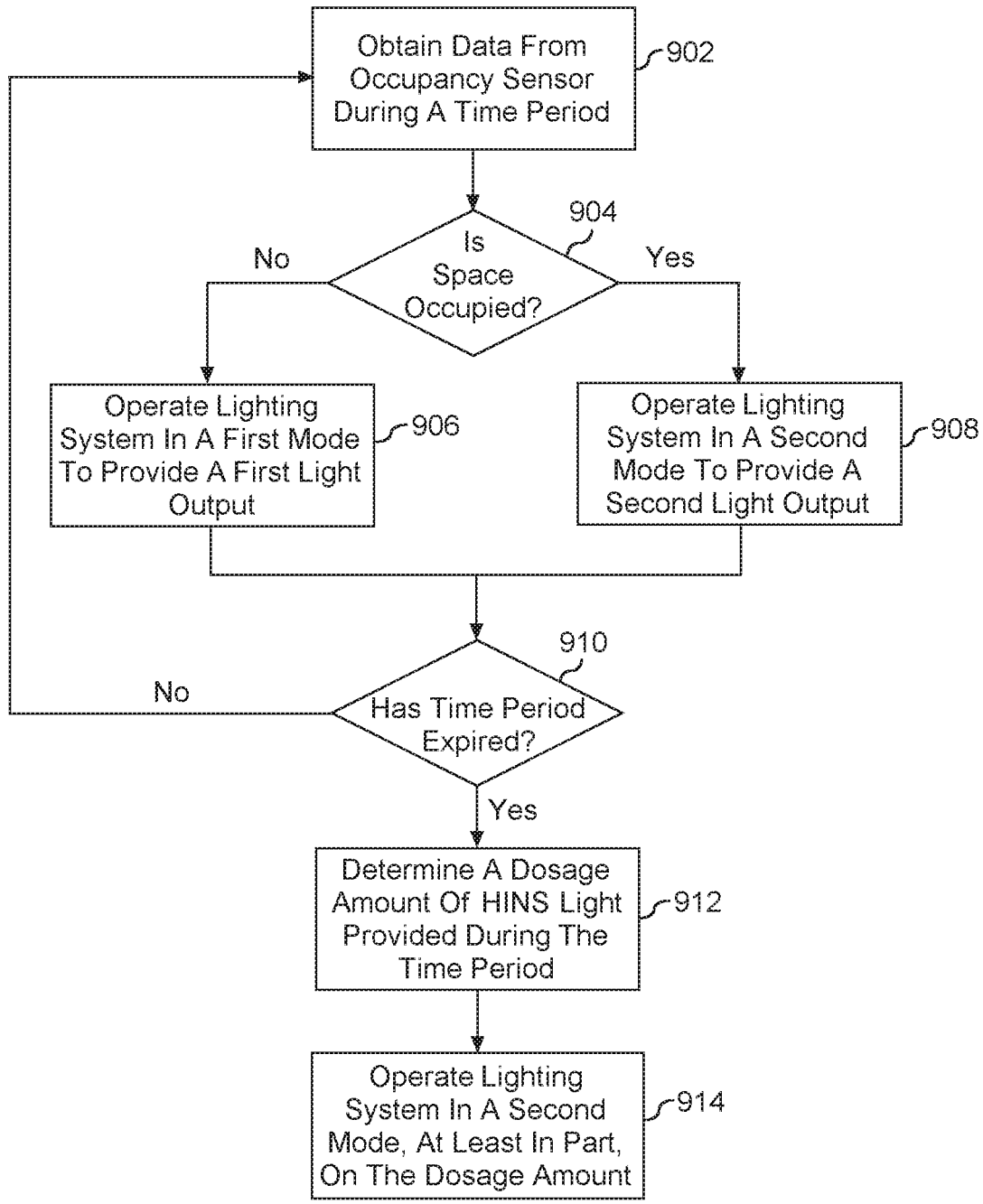
FIG. 9 depicts a flow diagram of a method for controlling operation of a lighting system according to example embodiments of the present disclosure.

Referring again to FIG. 5, the method 500 for controlling operation of the lighting system can include, at (508), operating the lighting system to provide the second light output. In some implementations, the second lighting output can be HINS light. In alternative implementations, the second light output can be a blend of HINS light and non-HINS light. As will Referring now to FIG. 9, another example method 900 for controlling operation of a lighting system is provided according to example embodiments of the present disclosure. The method 900 can be implemented by, for instance, the one or more control devices 160 of the lighting system 100 discussed above with reference to FIG. 1. FIG. 9 depicts steps performed in a particular order for purposes of illustration and discussion. Those of ordinary skill in the art, using the disclosures provided herein, will understand that various steps of any of the methods disclosed herein can be omitted, rearranged, expanded, adapted, and/or modified in various ways without deviating from the scope of the present disclosure.

At (902), the method 900 can include obtaining, by one or more control devices, data from an occupancy sensor during a time period. In some implementations, the time period can correspond to a user-defined time period. For instance, the user-defined time period can span normal business hours (e.g., about 9 AM to about 5 PM). It should be appreciated, however, that the user-defined time period can span any suitable amount of time.

At (904), the method 900 can include determining, by the one or more control devices, whether a space illuminated by the lighting system is occupied by one or more persons based, at least in part, on the data obtained at (902). When the data obtained at (902) indicates the space is occupied by one or more persons, the method 900 proceeds to (906). Otherwise, the method 900 proceeds to (908).

At (906), the method 900 can include operating the lighting system in a first mode to provide a first light output. In some implementations, the first light output can be a blend of HINS light and non-HINS light. For example, the HINS light can be emitted via one or more first light sources of the lighting system, whereas the non-HINS light can be emitted via one or more second light sources of the lighting system.

At (908), the method 900 includes operating the lighting system in a second mode to provide a second light output. In some implementations, the second light output can be HINS light. Alternatively, the second light output can be a blend of HINS light and non-HINS light.

At (910), the method 900 can include determining, by the one or more control devices, whether the time period has expired. If the one or more control devices determine the time period has expired, the method 900 proceeds to (912). Otherwise, the method 900 reverts to (902). It should be appreciated that multiple iterations of steps (902) to (910) can be performed during the time period. In this manner, the lighting system can switch between the first mode and the second mode to account for one or more persons entering and exiting the space illuminated by the lighting system during the time period.

At (912), the method 900 can include determining, by the one or more control devices, a dosage amount of light provided during the time period. In some implementations, the one or more control devices can implement the process described above with reference to FIG. 6 to determine the dosage amount of HINS light. In alternative implementations, the one or more control devices can implement the process described above with reference to FIG. 7 to determine the dosage amount of HINS light. In implementations in which operation of the lighting system switches between the first mode and the second mode one or more times during the time period, the one or more control devices can be configured to determine a total dosage amount associated with the first light output and the second light output during the time period.

At (914), the method 900 can include operating the lighting system in a second mode to provide a second light output based, at least in part, on the dosage amount determined at (912). The second light output can include HINS light or a blend of HINS light. Furthermore, the spectral energy associated with HINS light included in the second light output can be greater than the spectral energy associated with the HINS light included in the first light output. For instance, in some implementations, the spectral energy associated with the HINS light in the first light output can be less than about 20% of a total spectral energy associated with the first light output. Conversely, the spectral energy associated with HINS light in the second light output can be about 100% of a total spectral energy associated with the second light output.

Figure 10:
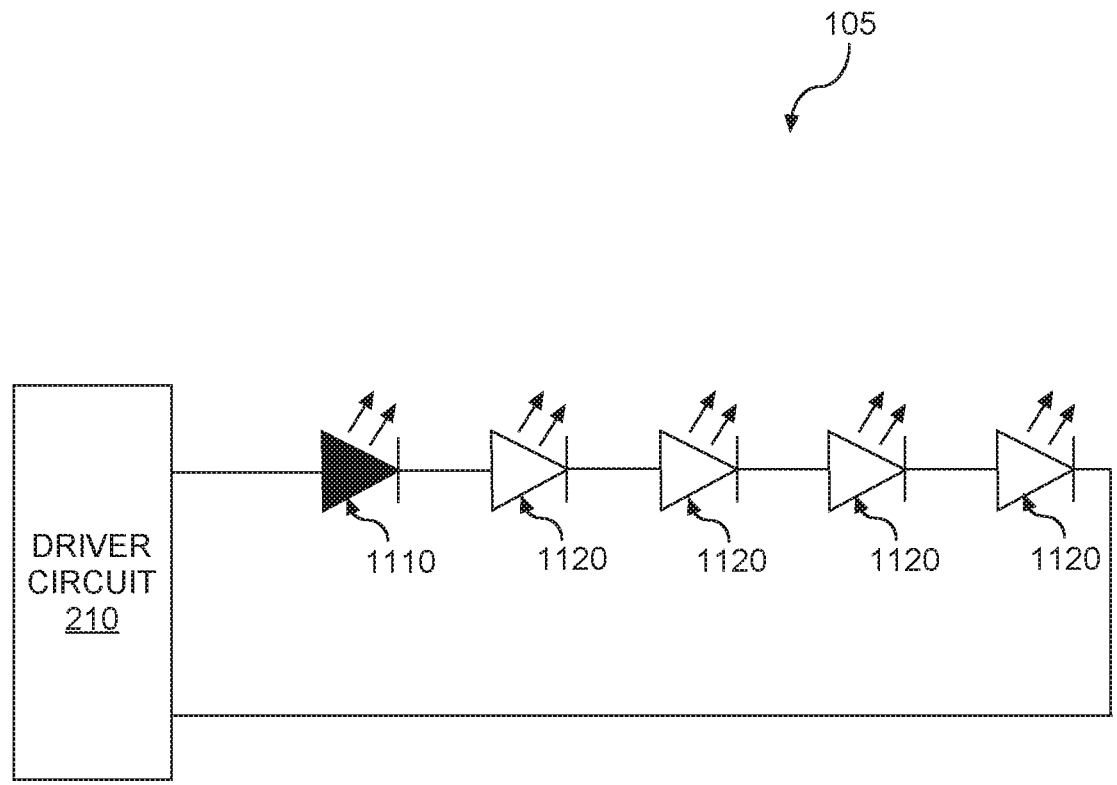
FIG. 10 depicts components of an example lighting fixture of a lighting system according to example embodiments of the present disclosure.

Referring now to FIG. 10, another example lighting fixture 105 of a lighting system is provided according to the present disclosure. The lighting fixture 105 can include a driver circuit 210 configured to receive an input current and provide an output current to one or more strings of light sources. Each string can include one or more light sources (e.g., LED light sources) coupled in series. Each string can include both HINS light sources and non-HINS light sources. In this manner, the lighting fixture 105 can emit a blend of HINS light and non-HINS light.

In some implementations, the driver circuit 210 of the lighting fixture 105 can be configured to provide the output current to an array of light sources. The array of light sources can include multiple strings of light sources coupled in parallel to one another. For example, the array of light sources can include seven strings of light sources coupled in parallel to one another. It should be appreciated, however, that the array of light sources can include more or fewer strings of light sources. For instance, in some implementations, the array of light sources can include five strings of light sources arranged in a parallel configuration. It should also be appreciated that each of the strings included in the array can include any suitable number of light sources coupled in series. For instance, in some implementations, each string can include twelve light sources coupled in series.

In some implementations, three of the twelve light sources included in a string of the array can be HINS light sources configured to emit HINS light. Conversely, the remaining light sources included in the string can be non-HINS light sources configured to emit non-HINS light. For instance, a color temperature of the non-HINS light emitted from the non-HINS light sources can correspond to a color temperature associated with white light. In some implementations, the spectral energy associated with HINS light emitted by the lighting fixture 105 can be less than about 20% of a total spectral energy associated with the light emitted by the lighting fixture. For instance, the spectral energy associated with HINS light emitted by the lighting fixture 105 can be between about 13% and 18% of the total spectral energy.

In some implementations, the HINS light sources included in a string of the array can be spaced apart from one another. For instance, two or more non-HINS light sources 1120 can be coupled between consecutive HINS light sources 1110 in the string. In this manner, there can be two or more non-HINS light sources 1120 positioned between consecutive HINS light sources 1110 in the string. It should be appreciated, however, that any suitable number of non-HINS light sources 1120 can be coupled between consecutive HINS light sources 1110 in the string.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A method for controlling operation of a lighting system, the method comprising:
   operating the lighting system in a first mode to provide a first light output during a time period, the first light output comprising a blend of high intensity narrow spectrum (HINS) light and non-HINS light emitted;
   determining, by one or more control devices, a dosage amount of HINS light provided during the time period;
   operating the lighting system in a second mode to provide a second light output based, at least in part, on the dosage amount, the second light output comprising HINS light or a blend of HINS light and non-HINS light,
      wherein spectral energy associated with HINS light in the second light output is greater than spectral energy associated with the HINS light in the first light output;
   determining, by the one or more control devices, a difference between the dosage amount and a threshold dosage amount; and
   determining, by the one or more control devices, a duration to provide the second light output based, at least in part, on the difference between the dosage amount and the threshold amount.

2. The method of claim 1, wherein determining a dosage amount of HINS light provided during the time period comprises:
   determining, by the one or more control devices, a duration the lighting system provides the first light output during the time period;
   determining, by the one or more control devices, an intensity of the HINS light provided as part of the first light output during the time period; and
   determining, by the one or more control devices, the dosage amount based, at least in part, on the duration and the intensity.

3. The method of claim 1, wherein determining a dosage amount of HINS light provided during the time period comprises:
   obtaining, by the one or more control devices, data from a dosage feedback sensor; and
   determining, by the one or more control devices, the dosage amount based, at least in part, on the data obtained from the dosage feedback sensor.

4. The method of claim 1, wherein determining the duration to provide the second light output further comprises:
   determining, by the one or more control devices, the duration to provide the second light output as a function of intensity of the HINS light provided as part of the second light output and the difference between the dosage amount and the threshold dosage amount.

5. The method of claim 1, wherein the spectral energy associated with the HINS light in the first light output is less than about 20% of a total spectral energy associated with the first light output.

6. The method of claim 1, wherein the spectral energy associated with the HINS light in the second light output is about 100% of a total spectral energy associated with the second light output.

7. The method of claim 1, further comprising:
   obtaining, by the one or more control devices, data from an occupancy sensor during the time period, the occupancy sensor associated with a space illuminated by the lighting system; and
   controlling, by the one or more control devices, operation of the lighting system based, at least in part, on the data obtained from the occupancy sensor.

8. The method of claim 7, wherein when the data obtained from the occupancy sensor indicates presence of one or more persons within the space, controlling operation of the lighting system comprises:

operating the lighting system in the first mode to provide the first light output.

9. The method of claim 7, wherein when the data obtained from the occupancy sensor indicates one or more persons are not present within the space, controlling operation of the lighting system comprises:
   operating the lighting system in the second mode to provide the second light output.

10. The method of claim 7, wherein when operation of the lighting system switches between the first mode and the second mode during the time period, determining a dosage amount of HINS light provided during the time period comprises:
    determining, by the one or more control devices, a total dosage amount associated with the first light output and the second light output during the time period.

11. The method of claim 1, wherein:
    a wavelength of HINS light is within a range of about 380 nanometers to about 420 nanometers; and
    a wavelength of non-HINS light is outside the range of about 380 nanometers to about 420 nanometers.

12. The method of claim 11, wherein the wavelength of the HINS light corresponds to about 405 nanometers.

13. The method of claim 1, wherein the dosage amount is determined for a surface illuminated by the lighting system.

14. The method of claim 13, wherein the dosage amount is determined as a function of distance between the surface and one or more light sources of the lighting system.

15. A lighting system, comprising:
    one or more first light sources configured to emit high intensity narrow spectrum (HINS) light;
    one or more second light sources configured to emit at least non-HINS light; and
    one or more control devices configured to:
       operate the lighting system in a first mode to provide a first light output during a time period, the first light output comprising a blend of the HINS light emitted from the one or more first light sources and non-HINS light emitted from the one or more second light sources;
       determine a dosage amount of HINS light provided during the time period;
       operate the lighting system in a second mode to provide a second light output based, at least in part, on the dosage amount, the second light output comprising HINS light or a blend of HINS light and non-HINS light,
          wherein spectral energy associated with HINS light in the second light output is greater than spectral energy associated with the HINS light in the first light output;
       determining, by the one or more control devices, a difference between the dosage amount and a threshold dosage amount; and
       determining, by the one or more control devices, a duration to provide the second light output based, at least in part, on the difference between the dosage amount and the threshold amount.

16. The lighting system of claim 15, wherein:
    the one or more second light sources comprise a plurality of strings arranged in a parallel configuration;
    each of the plurality of strings includes a plurality of HINS light sources and a plurality of non-HINS light sources; and
    at least one string of the plurality of strings includes two or more non-HINS light sources positioned between consecutive HINS light sources of the at least one string.

17. The lighting system of claim 15, wherein the one or more control devices are configured to determine the dosage amount provided during the time period based, at least in part, on:
    a duration the lighting system provides the first light output during the time period; and an intensity of the HINS light provided as part of the first light output during the time period.

18. The lighting system of claim 15, wherein the one or more control devices are further configured to:
    determine a duration to provide the second light output based, at least in part, on the dosage amount.

* * * * *